(12) United States Patent
Ulrich

(10) Patent No.: US 6,673,786 B1
(45) Date of Patent: Jan. 6, 2004

(54) TRYPTASE INHIBITORS

(75) Inventor: Wolf-Rüdiger Ulrich, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/049,111

(22) PCT Filed: Aug. 9, 2000

(86) PCT No.: PCT/EP00/07720

§ 371 (c)(1),
(2), (4) Date: May 3, 2002

(87) PCT Pub. No.: WO01/10848

PCT Pub. Date: Feb. 15, 2001

(30) Foreign Application Priority Data

Aug. 10, 1999 (EP) .............................. 99115737

(51) Int. Cl.⁷ .................... C07D 245/02; A61K 31/395
(52) U.S. Cl. ................... 514/183; 514/252.11; 540/460
(58) Field of Search ......................... 540/460; 514/183, 514/252.11

(56) References Cited

U.S. PATENT DOCUMENTS 6,022,969 A   2/2000   Rice et al. ................... 544/357
6,211,228 B1  4/2001   Rice et al. ................... 514/450

FOREIGN PATENT DOCUMENTS

WO   96/09297   3/1996
WO   98/04537   2/1998
WO   99/40083   12/1999

*Primary Examiner*—Bruck Kifle
(74) *Attorney, Agent, or Firm*—Nath & Associates PLLC; Todd L. Juneau; Sheldon M. McGee

(57) ABSTRACT

A compound of formula I

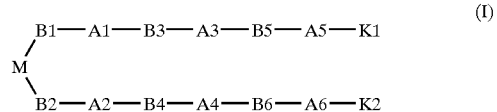

in which M, A1, A2, A3, A4, A5, A6, B1, B2, B3, B4, B5, B6, K1, and K2 are defined herein and are novel effective tryptase-inhibitors.

5 Claims, No Drawings

TRYPTASE INHIBITORS

FIELD OF APPLICATION OF THE INVENTION

The invention relates to novel tryptase inhibitors which are used in the pharmaceutical industry for preparing medicaments.

KNOWN TECHNICAL BACKGROUND

The international applications WO95/32945, WO96/09297, WO98/04537, WO99/12918 and WO99/24395 describe low-molecular-weight compounds for use as tryptase inhibitors.

DESCRIPTION OF THE INVENTION

It has now been found that the compounds of the formula I, which are described in more detail below, have surprising and particularly advantageous properties.

The invention provides compounds of the formula I

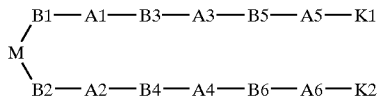

(I)

in which

A1 and A2 are identical or different and are —C(O)—, —NH—, —O— (oxygen), —S— (sulfur), —S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —O—, —S—, —NH—, —O—C(O)—, —C(O)—O—, —C(O)—NH—, —NH—C(O)— or a bond, or are selected from the group consisting of

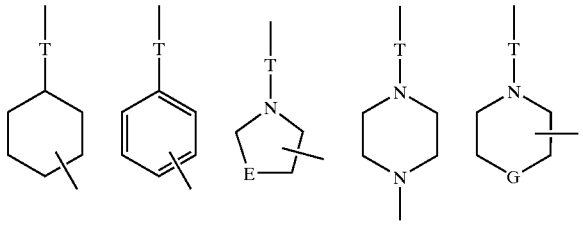

where

E is —O— (oxygen), —S— (sulfur) or —CH$_2$— (methylene),

G is —O— (oxygen) or —CH$_2$— (methylene), and

T is the group —C(O)— or a bond,

A5 and A6 are identical or different and are —C(O)—, —NH—, —O—, —S—, —C(O)—NH—, —NH—C(O)—, —O—C(O)—, —C(O)—O—, —NH—C(O)—NH— or a bond, M is the following central building block

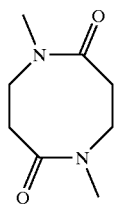

K1 is —B7-(C(O))$_m$—B9-X1, —B7-(C(O))$_m$—B9-Y1 or —B7-(C(O))$_m$—B9-Z1-B11-X1,

K2 is —B8-(C(O))$_p$—B10-X2, —B8-(C(O))$_p$—B10-Y2 or —B8-(C(O))$_p$—B10-Z2-B12-X2,

B1, B2, B3, B4, B5 and B6 are identical or different and are a bond or 1–4C-alkylene, B7, B8, B9, B10, B11 and B12 are identical or different and are a bond or 1–4C-alkylene, m is 0 or 1, p is 0 or 1, X1 and X2 are identical or different and are selected from the following groups

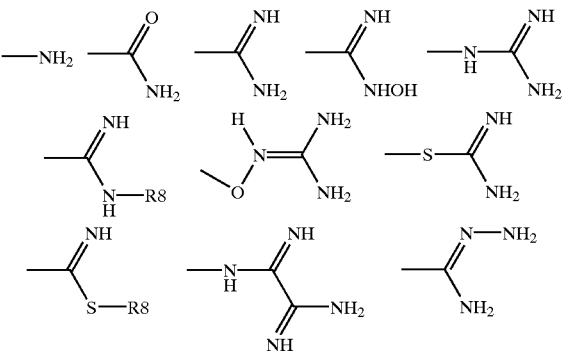

where

R8 is 1–4C-alkyl,

Y1 and Y2 are identical or different and are a 4–11C-heteroaryl or 2–7C-heterocycloalkyl radical containing at least one ring nitrogen, Z1 and Z2 are identical or different and are 5–12C-arylene, 5–12C-heteroarylene, 3–8C-cycloalkylene 3–8C-heterocycloalkylene, where each arylene, heteroarylene, cycloalkylene, heterocycloalkylene, heteroaryl or heterocycloalkyl may additionally for its part be substituted by one, two or three substituents selected from the group consisting of hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, and where on the direct route between the terminal nitrogen atoms 20 to 40, preferably 25 to 40, bonds have to be present, the salts of these compounds, and the N-oxides of the nitrogen-containing heteroaryls, heterocycloalkyls, heteroarylenes and heterocycloalkylenes, and their salts, where all those compounds are excluded in which one or more of the variables B1, B2, B3, B4, B5, B6, B7, B8, B9, B10, B11 or B12 may assume the meaning of a bond resulting in the direct linkage of two heteroatoms or two carbonyl groups.

1–4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and the methyl radicals.

1–4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

1–4C-Alkoxycarbonyl represents a carbonyl group to which is attached one of the above-mentioned 1–4C-alkoxy radicals. Examples which may be mentioned are the methoxycarbonyl [$CH_3O-C(O)-$] and the ethoxycarbonyl [$CH_3CH_2O-C(O)-$] radicals.

1–4C-Alkylcarbonyloxy represents a carbonyloxy group to which is attached one of the above-mentioned 1–4C-alkyl radicals. An example which may be mentioned is the acetoxy [$CH_3C(O)-O-$] radical.

For the purpose of the invention, halogen is bromine, chlorine and fluorine.

1–4C-Alkylene represents straight-chain or branched 1–4C-alkylene radicals, for example the methylene ($-CH_2-$), ethylene ($-CH_2-CH_2-$), trimethylene ($-CH_2-CH_2-CH_2-$), tetramethylene ($-CH_2-CH_2-CH_2-CH_2-$), 1,2-dimethylethylene [$-CH(CH_3)-CH(CH_3)-$], 1,1-dimethylethylene [$-C(CH_3)_2-CH_2-$], 2,2-dimethylethylene [$-CH_2-C(CH_3)_2-$], isopropylidene [$-C(CH_3)_2-$] or the 1-methylethylene [$-CH(CH_3)-CH_2-$] radicals.

If m is 0, the group $-(C(O))_m-$ is a bond.
If p is 0, the group $-(C(O))_p-$ is a bond.

4–11C-Heteroaryl represents a—if desired substituted—mono- or bicyclic aromatic hydrocarbon which contains 4 to 11 carbon atoms and at least one ring nitrogen atom; in addition, one or more of the carbon atoms may be replaced by ring heteroatoms selected from the group consisting of O, N and S. In the case of bicycles, at least one of the rings is aromatic. Examples which may be mentioned are pyrid-4-yl, pyrid-3-yl, pyrimidin-5-yl, imidazol-1-yl and benzimidazol-5-yl.

2–7C-Heterocycloalkyl represents a—if desired substituted—monocyclic saturated or partially saturated hydrocarbon which contains 2 to 7 carbon atoms and at least one ring nitrogen atom; in addition, one or more carbon atoms may be replaced by ring heteroatoms selected from the group consisting of O, N and S. Examples which may be mentioned are piperid4-yl, piperazin-1-yl, pyrrolidin-2-yl, pyrrolidin-3-yl, imidazolidin-1-yl, imidazolidin-2-yl, lmidazolidin-4-yl and morpholin-2-yl.

5–12C-Arylene represents a—if desired substituted—divalent mono- or bicyclic aromatic hydrocarbon radical having 5 to 12 carbon atoms, where in the case of bicyclic aromatic hydrocarbon radicals at least one of the rings is aromatic. The free valencies can both be located at the aromatic, both at the nonaromatic or one at the aromatic and one at the nonaromatic ring. Examples which may be mentioned are 1,4-phenylene, 1,3-phenylene, 1,4-naphthylene and 2,6-naphthylene.

5–12C-Heteroarylene represents an arylene radical as defined above in which 1 to 4 carbon atoms are replaced by heteroatoms selected from the group consisting of O, N and S. Examples which may be mentioned are 2,5-furylene, 2,5-pyrrolylene, 4,2-pyridylene, 5,2-pyridylene, 2,5-indolylene, 2,6-indolylene, 3,5-indolylene, 3,6-indolylene, 3,5-indazolylene, 3,6-indazolylene, 2,5-benzofuranylene, 2,6-quinolinylene and 4,2-thiazolylene.

3–8C-Cycloalkylene represents a—if desired substituted—divalent monocyclic saturated or partially saturated hydrocarbon radical having 3 to 8 carbon atoms. Examples which may be mentioned are the 1,3-cyclopentylene, the 1,3-cyclohexylene and preferably the 1,4-cyclohexylene radicals.

3–8C-Heterocycloalkylene represents a cycloalkylene radical as defined above in which 1 to 3 carbon atoms are replaced by heteroatoms selected from the group consisting of O, N and S. Examples which may be mentioned are the 1,4-piperidinylene, 1,4-piperazinylene, 2,5-pyrrolidinylene, 4,2-imidazolidinylene and preferably the 4,1-piperidinylene radicals.

Preferred meanings of the groups X1 and X2 are amino, aminocarbonyl, amidino and guanidino.

By definition, the groups Z1 and Z2 are located between the groups B9 and B11 (—B9-Z1-B11-) and B10 and B12 (—B10-Z2-B12-), respectively. Accordingly, in the divalent groupings mentioned by way of example (for example 2,6-indolylene), the first number indicates the point of attachment to the group B9 and B10, respectively, and the second number indicates the point of attachment to the group B11 and B12, respectively.

The definitions of M, A3, A4, X1 and X2 contain chemical formulae, such as, for example,

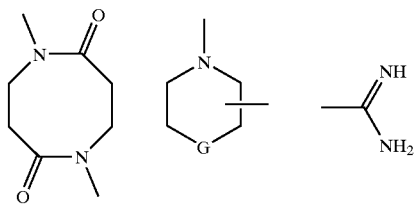

Here, bonds which are unattached on one side mean that the building block is attached at this site to the remainder of the molecule. Bonds which are unattached on both sides mean that this building block has a plurality of sites via which the building block can be attached to the remainder of the molecule.

In the context of this application, the term terminal nitrogen atom means in each case a nitrogen atom in the groups designated X1, X2, Y1 and Y2.

If the group X1 or X2 contains only one nitrogen atom, this nitrogen atom is the terminal nitrogen atom.

If the group X1 or X2 contains a plurality of nitrogen atoms, the nitrogen atom which is furthest from the atom by means of which the bond to the group B9 (B11) or B10 (B12) is established is the terminal nitrogen atom.

If the group Y1 or Y2 contains only one ring nitrogen atom, this ring nitrogen atom is the terminal nitrogen atom.

If the group Y1 or Y2 contains a plurality of ring nitrogen atoms, the ring nitrogen atom which is furthest from the atom by means of which the bond to the group B9 or B10 is established is the terminal nitrogen atom.

According to the invention, the direct route between the nitrogen atoms which act as terminal nitrogen atoms in the groups defined as X1 (Y1) or X2 (Y2) is considered to be the number of bonds which is obtained by counting the bonds which represent the shortest possible connection between the terminal nitrogen atoms.

The following example is meant to illustrate the determination of the number of bonds on the direct route between two terminal nitrogen atoms:

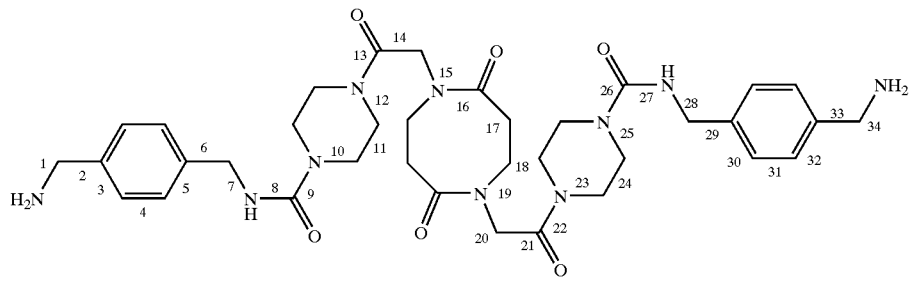

Here, the direct route comprises 34 bonds.

Suitable salts for compounds of the formula I—depending on substitution—are all acid addition salts or all salts with bases. Particular mention may be made of the pharmacologically acceptable salts of inorganic and organic acids customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically unacceptable salts which can be obtained initially as process products, for example in the preparation of the compounds according to the invention on an industrial scale, are converted into pharmacologically acceptable salts by processes known to the person skilled in the art.

It is known to the person skilled in the art that the compounds according to the invention, and also their salts, may contain varying amounts of solvents, for example when they are isolated in crystalline form. The invention therefore also embraces all solvates and in particular all hydrates of the compounds of the formula I, and also all solvates and in particular all hydrates of the salts of the compounds of the formula I.

Compounds of the formula I which are to be emphasized are those in which

A1 and A2 are identical or different and are —C(O)—, —NH—, —O—, —C(O)—NH—, —NH—C(O)—, —O—C(O)—, —C(O)—O— or a bond, A3 and A4 are identical or different and are —C(O)—, —O—, —NH—, —O—C(O)—, —C(O)—O—, —C(O)—NH—, —NH—C(O)— or a bond, or are selected from the group consisting of

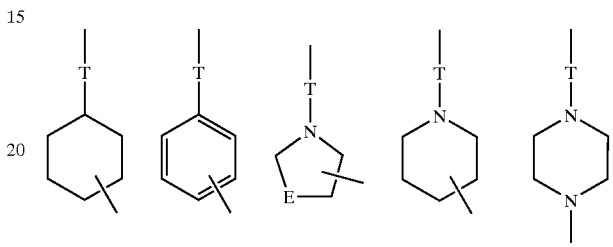

where

E is —O— (oxygen), —S— (sulfur) or —CH$_2$— (methylene) and

T is the group —C(O)— or a bond,

A5 and A6 are Identical or different and are —C(O)—, —NH—, —O—, —C(O)—NH—, —NH—C(O)—, —O—C(O)—, —C(O)—O—, —NH—C(O)—NH— or a bond, M is the following central building block

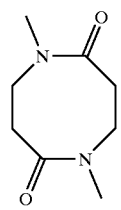

K1 is —B7-(C(O))$_m$—B9-X1, —B7-(C(O))$_m$—B9-Y1 or —B7-(C(O))$_m$—B9-Z1-B11-X1.

K2 is —B8-(C(O))$_p$—B10-X2, —B8-(C(O))$_p$—B10-Y2 or —B8-(C(O))$_p$—B10-Z2—B12-X2,

B1, B2, B3, B4, B5 and B6 are identical or different and are a bond or 1–4C-alkylene, B7, B8, B9, B10, B11 and B12 are identical or different and are a bond or 1–4C-alkylene, m is 0 or 1, p is 0 or 1, X1 and X2 are Identical or different and are selected from the following groups

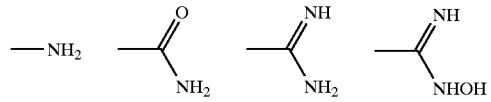

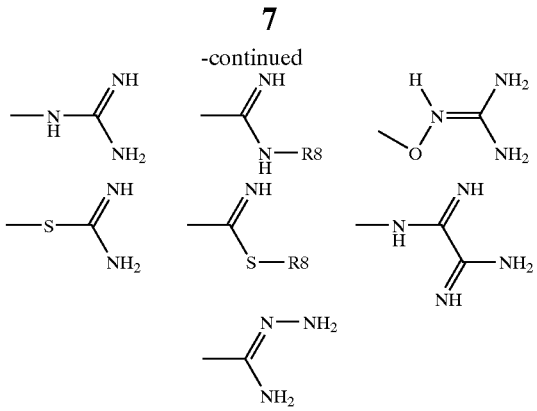

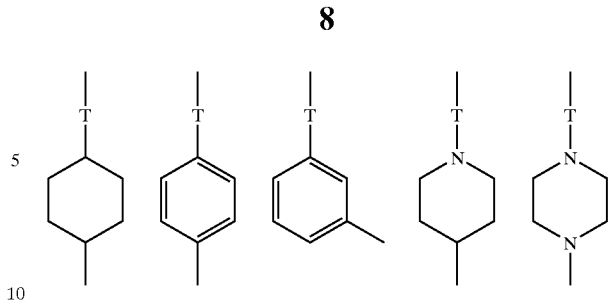

where

RB is 1–4C-alkyl,

Y1 and Y2 are identical or different and are piperid-4-yl, piperid-3-yl, piperazin-1-yl, piperazin-2-yl, morpholin-2-yl, pyrrolidin-2-yl, pyrrolidin-3-yl, imidazolidin-1-yl, imidazolidin-2-yl, imidazolidin-4-yl, 2-imidazolin-3-yl, 2-imidazolin-2-yl, imidazol-1-yl, imidazol-2-yl, imidazol-4-yl, pyrid-4-yl, pyrid-3-yl, pyridazin-4-yl, pyrimidin-5-yl, pyrimidin-4-yl, indol-3-yl, benzimidazol-4-yl or benzimidazol-5-yl, Z1 and Z2 are identical or different and are 1,4-phenylene, 1,3-phenylene, 1,4-naphthylene, 2,6-naphthylene, 1,4-cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene, where each arylene, heteroarylene, cycloalkylene, heterocycloalkylene, heteroaryl or heterocycloalkyl may additionally for its part be substituted by one, two or three substituents selected from the group consisting of hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, and where on the direct route between the terminal nitrogen atoms 20 to 40, preferably 25 to 40, bonds have to be present, the salts of these compounds, and the N-oxides of the nitrogen-containing heteroaryls, heterocycloalkyls, heteroarylenes and heterocycloalkylenes, and their salts, where all those compounds are excluded in which one or more of the variables B1, B2, B3, B4, B5, B6, B7, B8, B9, B10, B11 or may assume the meaning of a bond, resulting in the direct linkage of two heteroatoms or carbonyl groups.

One embodiment of the compounds of the formula I which are to be emphasized is that in which A1 and A2 are identical or different and are —C(O)—NH—, —C(O)— or a bond, A3 and A4 are identical or different and are selected from the group consisting of

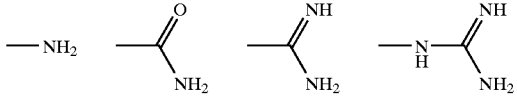

where

T is the group —C(O)— or a bond,

A5 and A6 are identical or different and are —O—, —C(O)—, —C(O)NH—, —NH—C(O)— or —NH—C(O)—NH—, M is the following central building block

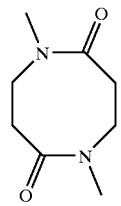

K1 is —B7-(C(O))$_m$—B9-Y1 or —B7-(C(O))$_m$—B9-Z1-B11-X1,

K2 is —B8-(C(O))$_p$—B10-Y2 or —B8-(C(O))$_p$—B10-Z2-B12-X2,

B1 and B2 are identical or different and are a bond or methylene,

B3, B4, B5 and B6 are identical or different and are a bond or 1–3C-alkylene,

B7, B8, B9 and B10 are identical or different and are a bond or 1–4C-alkylene,

B11 and B12 are identical or different and are a bond or methylene, m is 0, p is 0, X1 and X2 are identical or different and are selected from the following groups

—NH$_2$    NH$_2$)    NH$_2$)    —NH—C(NH)NH$_2$

Y1 and Y2 are imidazol-1-yl,

Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene, and where on the direct route between the terminal nitrogen atoms 20 to 40, preferably 25 to 40, bonds have to be present, the salts of these compounds, and the N-oxides of nitrogen-containing heteroaryls, heteroarylenes and heterocycloalkylenes, and their salts, where all those compounds are excluded in which one or more of the variables B1, B2, B3, B4, B5, B6, B7, B8, B9, B10, B11 or B12 may assume bond, resulting in the direct linkage of two heteroatoms or carbonyl groups.

Another embodiment of the compounds of the formula I which are to be emphasized is that in which A1 and A2 are identical or different and are —C(O)—, —C(O)—NH—, —C(O)—O— or a bond, A3 and A4 are identical or different and are 1,4-piperazinylene, 1,4-piperidinylene, 1,4-cyclohexylene, 1,3-phenylene or a bond, A5 and A6 are identical or different and are —C(O)—, —C(O)—NH—, —NH—C(O)— or —NH—C(O)—NH—, M is the following central building block

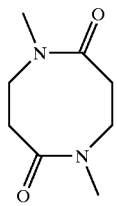

K1 is —B7-(C(O))$_m$—B9-Y1 or —B7-(C(O))$_m$—B9-Z1-B11-X1

K2 is B8-(C(O))$_p$—B10-Y2 or —B8-(C(O))$_p$,—B10-Z2-B12-X2,

B1 and B2 are identical or different and are a bond or methylene,

B3, B4, B5 and B6 are identical or different and are a bond or 1–3C-alkylene,

B7, B8, B9 and B10 are identical or different and are a bond or 1–4C-alkylene,

B11 and B12 are identical or different and are a bond or methylene, m is 0, p is 0, X1 and X2 are identical or different and are selected from the following groups

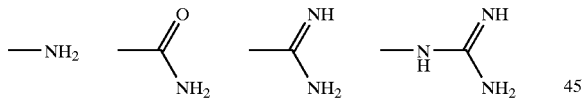

Y1 and Y2 are imidazol-1-yl,

Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene, and where on the direct route between the terminal nitrogen atoms 20 to 40, preferably 25 to 40, bonds have to be present, the salts of these compounds, and also the N-oxides of the nitrogen-containing heteroaryls, heteroarylenes and heterocycloalkylenes, and their salts, where all those compounds are excluded in which one or more of the variables B1, B2, B3, B4, B5, B6, B7, B8, B9, B10, B11 or B12 may assume the meaning of a bond, resulting in the direct linkage of two heteroatoms or carbonyl groups.

Preferred compounds of the formula I are those in which

—B1-A1-B3-A3-B5-A5- and —B2-A2-B4-A4-B6-A6- are identical or different from

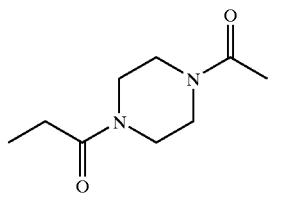

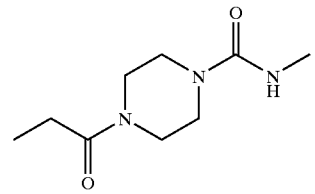

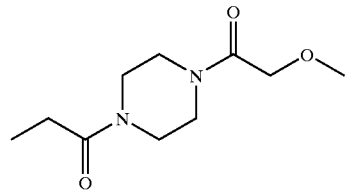

M is the following central building block

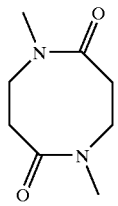

K1 is —B7-(C(O))$_m$—B9-Z1-B11-X1,

K2 is B8-(C(O))$_p$—B10-Z2-B12-X2,

B7, B8, B9 and B10 are identical or different and are a bond or methylene,

B11 and B12 are methylene, m is 0, p is 0,

X1 and X2 are amino,

Z1 and Z2 are identical or different and are 1,3-phenylene or 1,4-phenylene, and the salts of these compounds.

Particularly preferred compounds of the formula I are 1,5-Bis-{2-[4-[(4-aminomethylbenzylaminocarbonyl) piperazin-1-yl]-2-oxoethyl}-perhydro-1,5-diazocin-2,6-dione;

1,5-Bis-{2-[4-(3-(4-aminomethylphenyl)propionyl) piperazin-1-yl]-2-oxoethyl}perhydro-1,5-diazocin-2,6-dione;

1,5-Bis-{2-[4-(3-(3-aminomethylphenyl)propionyl) piperazin-1-yl]-2-oxoethyl}perhydro-1,5-diazocin-2,6-dione;

1,5-Bis-{2-[4-(2-(4-aminomethylphenoxy)acetyl) piperazin-1-yl]-2-oxoethyl}perhydro-1,5-diazocin-2,6-dione;

and the salts of these compounds.

The compounds of the formula I are constructed from a large number of divalent building blocks (M, A1, A2, A3, A4, A5, A6, B1, B2, B3, B4, B5, B6, B7, B8, B9, B10, B11, B12, Z1 and Z2). In principle they can be synthesized starting with any of these building blocks. If the compounds of the formula I are constructed largely symmetrically, it is favorable to start the synthesis with the central building block M, whereas in the case of predominantly asymmetrical compounds of the formula I a synthesis starting with one of the end groups K1 or K2 may be advantageous.

Here, the building blocks are linked using always the same pattern, known per se to the person skilled in the art.

It Is known to the person skilled in the art that the compounds of the formula I can either be synthe sized building block by building block, or by initially constructing relatively large fragments consisting of several individual building blocks, which can then be joined to give the complete molecule.

Owing to the meanings which the individual building blocks of the compounds of the formula I can assume, amino [—NH—], ether [—O—], thioether [—S—], keto [—C(O)—], sulfonyl [—S(O)$_2$—], ester [—O—C(O)—, —C(O)—O—], amide [—C(O)—NH—, —NH—C(O)—], sulfonamide [—SO$_2$—NH—, —NH—SO$_2$—], carbamate [—NH—C(O)—O—, —O—C(O)—NH—], carbamide [—NH—C(O)—NH—] or carbonate bridges [—O—C(O)—O—] are present in the compounds of the formula I.

How to prepare such bridges is known per se to the person skilled in the art; suitable methods and starting materials for their preparation are described, for example, in March, Advanced Organic Chemistry, Reactions, Mechanisms and Structure, Third Edition, 1985, John Wiley & Sons.

Ether and thioether bridges can be prepared, for example, by the method of Williamson.

Keto bridges can be introduced, for example, as a component of relatively large building blocks, such as, for example, 1,3-dichloroacetone.

Sulfonyl bridges can be obtained, for example, by oxidation of thioether bridges.

There is a large number of known methods for preparing ester bridges. An example which may be mentioned here is the reaction of acids with alcohols, preferably using H$_2$SO$_4$ or p-toluenesulfonic acid as catalyst; or with addition of a dehydrating agent, such as, for example, molecular sieve or a carbodiimide. Furthermore, the reaction of acyl chlorides with alcohols may be mentioned here.

There is also a large number of known methods for preparing amide bridges. An example which may be mentioned here is the reaction of acyl chlorides with primary or secondary amines. Furthermore, reference is also made to all the methods which have been developed for peptide chemistry. Accordingly, it is possible to construct sulfonamide bridges from sulfonyl chlorides and primary or secondary amines.

Carbamate bridges can be prepared, for example, by reacting chloroformates with amines. The chloroformates for their part can be synthesized from alcohols and phosgene. A further variant for constructing carbamate bridges is the addition of alcohols to isocyanates.

Similarly to the carbamate bridges, it is possible to prepare carbonate bridges starting from chloroformates, by reaction with alcohols (instead of amines).

Carbamide bridges can be prepared, for example, by reacting isocyanates with amines.

The preparation of compounds of the formula I may be shown in an exemplary manner using the reaction scheme below. Other compounds of the formula I can be prepared analogously, or by using the abovementioned methods known per se to the person skilled in the art.

Reaction scheme 1:

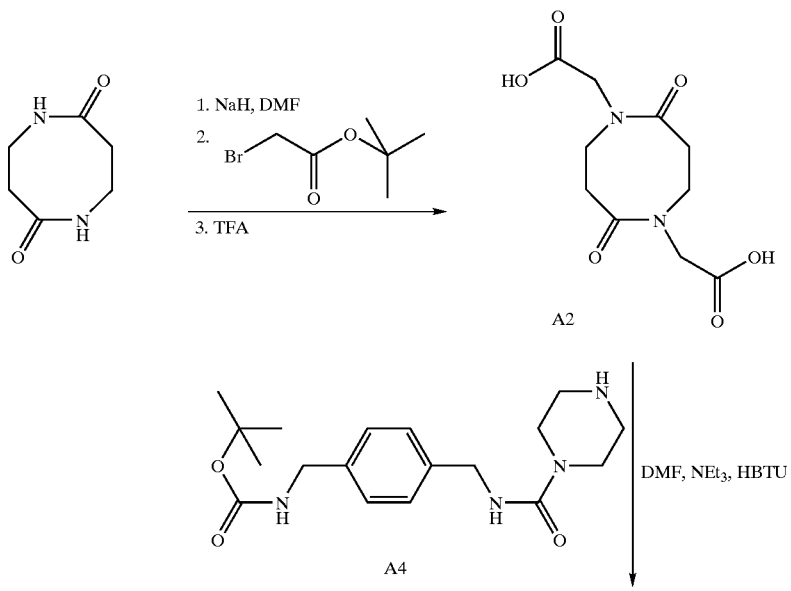

-continued

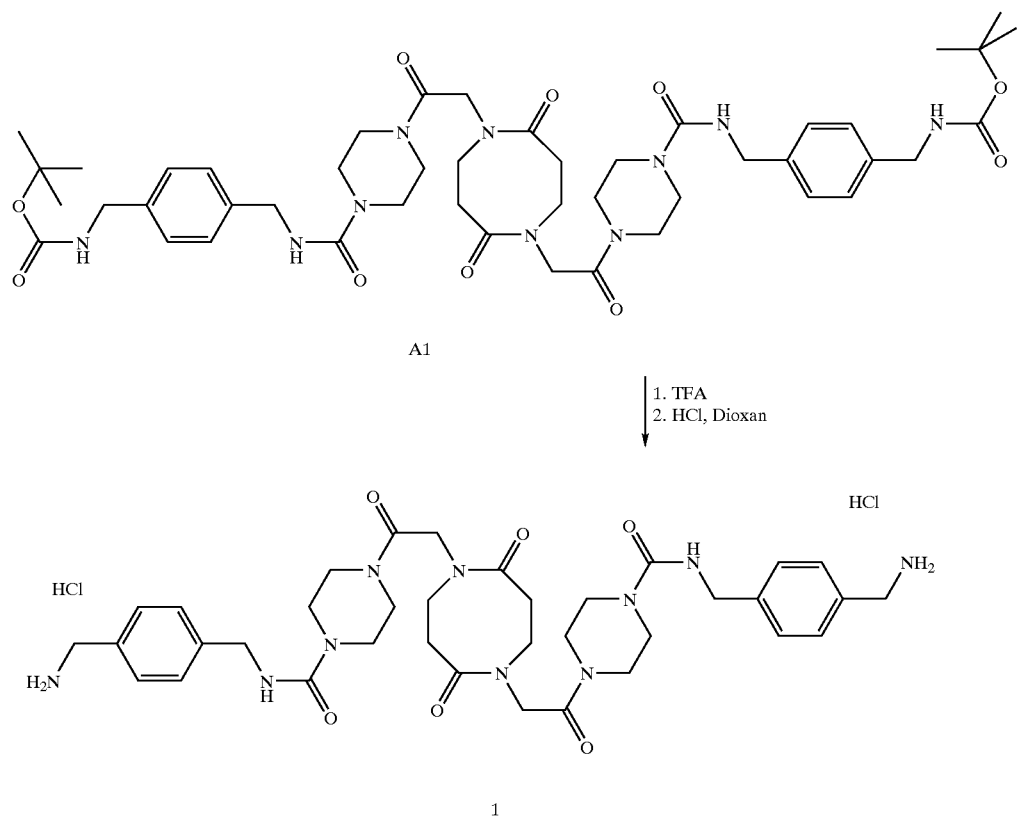

A1

1. TFA
2. HCl, Dioxan

1

Reaction scheme 1 shows an example of the synthesis of a compound of the formula I.

It is also possible to convert compounds of the formula I by derivatization into other compounds of the formula I. Thus, for example, compounds of the formula I having a nitrogen-containing heteroaryl, heteroarylene, heterocycloalkyl or heterocycloalkylene building block can be converted by oxidation into the corresponding N-oxides.

The N-oxidation is carried out in a manner which is likewise known to the person skilled in the art, for example using hydrogen peroxide in methanol or m-chloroperoxybenzoic acid in dichloromethane at room temperature. Which reaction conditions are required in the particular case for carrying out the process is known to the person skilled in the art owing to his expert knowledge.

It is furthermore known to the person skilled in the art that if there are a number of reactive centers on a starting material or intermediate, it may be necessary to block one or more reactive centers temporarily by protective groups in order to allow a reaction to proceed specifically at the desired reaction center. A detailed description of the use of a large number of proven protective groups is found, for example, in T. W. Greene, Protective Groups in Organic Synthesis, John Wiley & Sons, 1991.

The isolation and purification of the substances according to the invention is carried out in a manner known per se, for example by distilling off the solvent under reduced pressure and recrystallizing the resulting residue from a suitable solvent or subjecting it to one of the customary purification methods, such as, for example, column chromatography on a suitable support material.

Salts are obtained by dissolving the free compound in a suitable solvent (for example a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically unacceptable salts can be converted into pharmacologically acceptable salts.

The examples below serve to illustrate the invention in more detail without restricting it. Likewise, further compounds of the formula I, whose preparation is not explicitly described, can be prepared in an analogous manner or in a manner familiar per se to the person skilled in the art using customary process techniques.

In the examples below, the abbreviation RT stands for room temperature, h for hours, min. for minutes, DMF for dimethylformamide and HBTU for O-(benzotriazol-1-yl)-N,N,N',N'-tetramethyluronium hexa-fluorophosphate. The compounds mentioned in the examples and their salts are the preferred subject of the invention.

EXAMPLES

End Products

1. 1,5-bis-{2-[4-(4-Aminomethylbenzylaminocarbonyl)piperazin-1-yl]-2-oxoethyl}perhydro-1,5-diazocin-2,6-dione Dihydrochloride

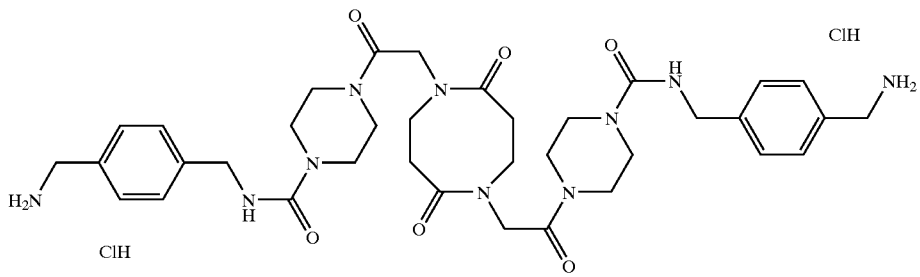

0.2 g of 1,5-bis-{2-[4-(4-tert-butyloxycarbonylaminomethylbenzylaminocarbonyl)piperazin-1-yl]-2-oxoethyl}-perhydro-1,5-diazocin-2,6-dione (starting material A1) is suspended in 2 ml of dichloromethane and then admixed with 2 ml of trifluoroacetic acid. The mixture is stirred at RT overnight, and 2 ml of a solution of HCl in dioxane are then added. The mixture is concentrated to dryness using a rotary evaporator. The residue is twice triturated with ether and the solvent decanted off. The residue is then dried under high vacuum. This gives 0.17 g of the title compound of m.p. from 90° C. (decomposition). The mass spectrum shows the molecular peak MH$^+$ at 719 Da.

2. 1,5-bis-{2-[4-(3-(4-aminomethylphenyl)proplonyl)piperazin-1-yl]-2-oxoethyl}perhydro-1,5-diazocin-2,6-dione Dihydrochloride

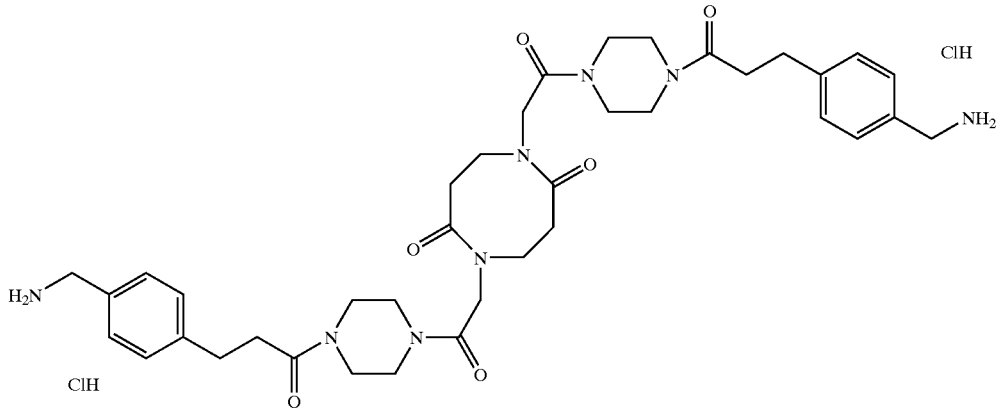

The title compound is prepared in analogy to example 1 from 0.08 g 1,5-bis-{2-[4-(3-(4-tert-butoxycarbonylaminomethylphenyl)propionyl)piperazin-1-yl]-2-oxoethyl}perhydro-1,5-diazocin-2,6-dione (starting material B1) in 2 ml dichloromethane/2 ml trifluoroacetic acid. Yield: 0.055 g; the mass spectrum shows the molecular peak MH$^+$ at 717 Da.

3. 1,5-bis-{2-[4-(3-(3-aminomethylphenyl)proplonyl)piperazin-1-yl]-2-oxoethyl}perhydro-1,5-diazocin-2,6-dione Dihydrochloride

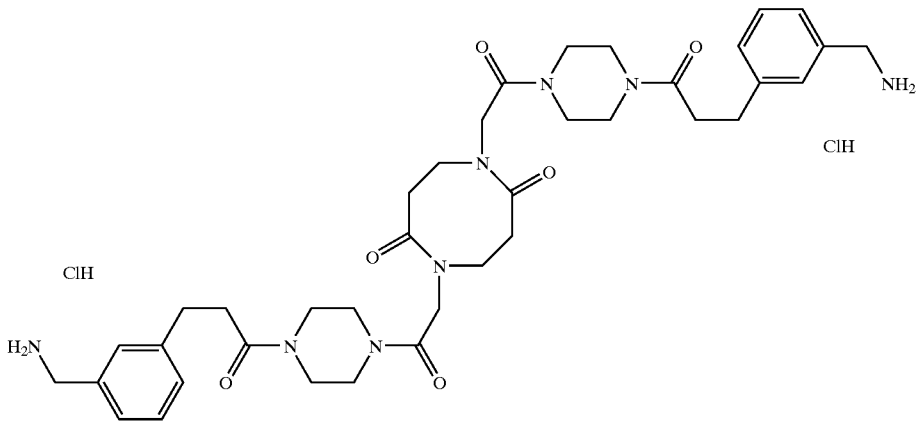

The title compound is prepared from 0.083 g 1,5-bis-{2-[4-(3-(3-tert-butoxycarbonylaminomethylphenyl)-propionyl)piperazin-1-yl]-2-oxoethyl}-1,5-diazocin-2,6-dione (starting material C1) as described in example 1. Yield: 0.063 g; mass spectrum: MH⁺=717 Da.

4. 1,5-bis-{2-[4-(2-(4-Aminomethylphenoxy)acetyl)perazin-1-yl]-2-oxoethyl}perhydro-1.5-diazocin-2,6-dione Dihydrochloride

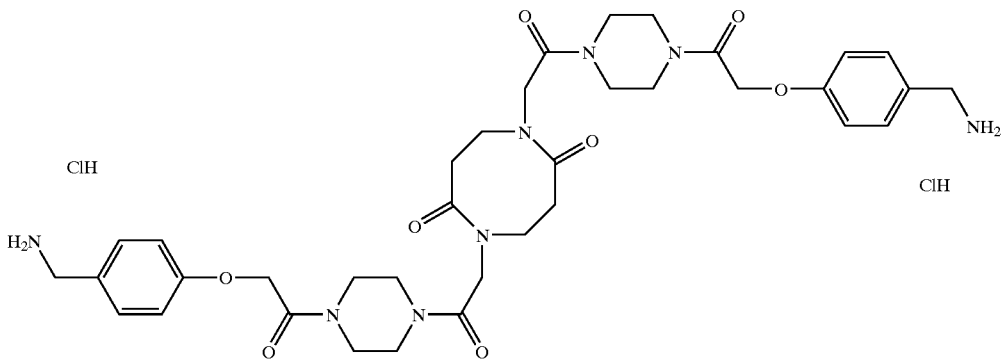

The title compound is prepared from 0.142 g 1,5-bis-{2-[4-(2-(4-tert-butoxycarbonylaminomethylphenoxyyacetyl)piperazin-1-yl-]-2-oxoethyl}-1,5-diazocin-2,6-dione (starting material D1) as described in example 1. Yield: 0.115 g; mass spectrum: MH⁺=721 Da.

Starting Materials

A1. 1,5-bis-{2-[4-(4-tert-Butyloxycarbonylaminomethylbenzylaminocarbonyl)piperazin-1-yl]-2-oxoethyl}perhydro-1,5-diazocin-2,6-dione A mixture of 0.538 ml of triethylamine in 10 ml of DMF is mixed successively with 0.4 g of (5-carboxy-methyl-2,6-dioxoperhydro-1,5-diazocin-1-yl)acetic acid (starting material A2) and 1.23 g of HBTU, with stirring. After one hour, 1.13 g of 1-[4-(tert-butyloxycarbonylaminomethyl)benzylamino-carbonyl]piperazine (starting material A4) are added, and the mixture is stirred overnight. The mixture is diluted with dichloromethane and admixed with water. After phase separation, the organic phase is washed with 1N hydrochloric acid solution, 1N aqueous sodium hydroxide solution and water. The organic phase is concentrated and the residue is triturated with acetone/ethyl acetate, filtered off with suction and recrystallized from methanol/ether. Drying under reduced pressure gives 0.75 g of the title compound of m.p. 156–160° C. The mass spectrum shows the molecular peak MH⁺ at 919 Da.

A2. (5-Carboxymethyl-2,6-dioxoperhydro-1,5-diazocin-1-yl)acetic Acid 1.4 g of tert-butyl-(5-tert-butoxycarbonylmethyl-2,6-dioxoperhydro-1,5-diazocin-1-yl)acetate (starting material A3) are dissolved in 6 ml of dichloromethane and admixed with 6 ml of trifluoroacefic acid. The mixture is stirred overnight and then concentrated using a rotary evaporator, and the residue is triturated with ethyl acetate/petroleum ether (1:1). The residue is filtered off with suction and dried under reduced pressure. This gives 0.89 g of the title compound of m.p. from 250° C. (decomposition). The mass spectrum shows the molecular peaks MH⁺ and MNH₄⁺ at 259 and 276 Da.

A3. tert-Butyl (5-tert-butoxycarbonylmethyl-2,6-dioxoperhydro-1,5-diazocin-1-yl)acetate 3.3 g of perhydro-1,5-diazocin-2,6-dione are suspended in 30 ml of absolute DMF, and 732 mg of sodium hydride (80%) are then added. The mixture is stirred at RT for 15 min and then cooled to 0° C., and 3.76 ml of tert-butyl bromoacetate are then added. The mixture is stirred at 0° C. for 15 min and at RT for 30 min, and is then once again cooled to 0° C., and another 732 mg of sodium hydride (80%) are added. After 15 min, a further 3.76 ml of tert-butyl bromoacetate are added using a pipette, the ice bath is removed after 15 min and the mixture stirred at RT overnight. The mixture is then diluted with dichloromethane, water is added, and the phases are then separated and the organic phase is washed twice with water. The organic phase is dried over MgSO$_4$ and concentrated, and the residue is dried under high vacuum and recrystallized from n-hexane. This gives 2.5 g of the title compound of m.p. 180° C. The mass spectrum shows the molecular peaks MH$^+$ and MNH$_4^+$ at 371 and 388 Da.

A4. 1-[4-(tert-Butyloxycarbonylaminomethyl) benzylaminocarbonyl]piperazine 41.7 g of benzyl 4-[4-(tert-butyloxycarbonylaminomethyl)benzylaminocarbonyl] piperazine-1-carboxylate (starting material A5) in 1.0 l of methanol are hydrogenated over palladium/carbon (5%) for 4 h. The catalyst is filtered off and the solvent is removed, giving 30.3 g of the title compound as a colorless oil.

A5. Benzyl 4-[4-(tert-Butyloxycarbonylaminomethyl) benzylaminocarbonyl]piperazine-1-carboxylate At 0° C., 25.0 g (106 mmol) of 4-(tert-butyloxycarbonylaminomethyl)benzylamine in 150 ml of dichloromethane are added dropwise to a solution of 22.4 g (111 mmol) of 4-nitrophenyl chloroformate in 200 ml of dichloromethane, and the mixture is stirred for 10 min. 15.6 ml (111 mmol) of triethylamine are then added dropwise, and the mixture is stirred at RT for 1.5 h. At 0° C., initially 24.5 g (111 mmol) of benzyl piperazine-1-carboxylate in 80 ml of dichloromethane and then 15.6 ml (111 mmol) of triethylamine are added dropwise. The mixture is stirred at RT for 16 h. The solvent is removed from the reaction mixture and the crude product is chromatographed over silica gel (toluene/ethyl acetate=1:1). Crystallization from diisopropyl ether gives 41.7 g of the title compound as a colorless solid of m.p. 108–112° C.

B1. 1,5-bis-{2-[4-(3-(4-tert-Butoxycarbonylaminomethylphonyloproplonyl)pirerazin-1-yl]-2-oxoethyl}perhydro-1,5-diazocin-2,6-dione A mixture of 0.3 ml of ethyldiisopropylamine in 4 ml of DMF is mixed successively with 0.15 g of (5-carboxymethyl-2,6-dioxoperhydro-1,5-diazocin-1-yl) acetic acid (starting material A2) and 0.463 g of HBTU with stirring. After 10 min, 0.404 g of 1-[3-(4-tert-butyloxycarbonylaminomethyl-phenyl)propionyl) piperazine (starting material B2) are added, and the mixture is stirred for 3 h. The mixture is diluted with dichloromethane and admixed with water. After phase separation, the organic phase is washed with 1N hydrochloric acid solution, 1N aqueous sodium hydroxide solution and water. After drying over magnesium sulfate, the organic solution is concentrated and the residue is chromatographed over silica gel (dichloromethane/methanol=9:1). Concentration of the pure fractions and drying in vacuo gives 0.29 g of the title compound as a colourless powder. The mass spectrum shows the molecular peaks MH$^+$ and MNa$^+$ at 917 and 939 Da.

B2. 1-[3-(4-tert-Butyloxycarbonylaminomethylphenyl) propionyl)piperazine 3.64 g of 1-benzyloxycarbonyl-4-[3-(4-tert-butyloxycarbonylaminomethylphenyl)propionyl]piperazine (starting material B3), dissolved in 100 ml methanol are hydrogenated over palladiumicarbon (10%) for 3 h. The catalyst is filtered off and the solvent is removed in vacuo, giving 2.55 g of the title compound. The mass spectrum shows the molecular peak MH$^+$ at 348 Da.

B3. 1-Benzyloxycarbonyl-4-[3-(4-tert-butyloxycarbonylaminomethylphenyl)propionyl]-piperazine A mixture of 11.4 ml of ethyldiisopropylamine in 20 ml of DMF is mixed successively with 3.11 g of 3-(4-tert-butyloxycarbonylaminomethylphenyl)propionic acid (starting material B4) and 4.64 g HBTU, with stirring. After ten minutes 2.45 g of 1-benzyloxycarbonylpiperazine are added and the mixture is stirred at RT for 5 h. The mixture is diluted with ethyl acetate and water. After phase separation, the organic phase is washed with 1N hydrochloric acid solution, 1N aqueous sodium hydroxide solution and water. After drying over magnesium sulfate, the organic solution is concentrated and the residue is chromatographed over silica gel (petrolether/ethyl acetate/acetone 4:5:1). Concentration of the pure fractions and drying in vacuo gives 3.91 g of the title compound as a yellowish powder. The mass spectrum shows the molecular peak MH$^+$ at 481.8 Da.

B4. 3-(4-tert-Butyloxycarbonylaminomethylphenyl) propionic Acid 4.65 g of methyl 3-4-aminomethylphenyl)propionate hydrochloride (starting material B5) and 6.17 ml of triethylamine are mixed in 20 ml of dichloromethane. To this mixture, a solution of 4.62 g of di-tert-butyl-dicarbonate in 10 ml of dichloromethane is added slowly at 0° C. with stirring. Stirring is continued 1 h at 0° C. and 3 h at RT. Then the reaction mixture is washed twice with 1N hydrochloric acid solution, with sodium hydrogen carbonate solution and water. After drying over magnesium sulfate, the solvent is removed and the residue (5.6 g) is dissolved in 50 ml of tetrahydrofurane. 13.4 ml of 2N aqueous sodium hydroxide solution is added and the mixture is stirred overnight, neutralized with 6.7 ml of 4N hydrochloric acid solution and the organic solvent is distilled off. The white precipitate is filtered by suction, washed with water and dried to give 4.65 g of the title compound. The mass spectrum shows the molecular peak MNH$_4^+$ at 297 Da.

B5. Methyl 3-(4-Aminomethylphenyl)propionate Hydrochloride 5.6 g of methyl 4-(hydroxyimino-methyl)cinnamate (starting material B6) are dissolved in a mixture of 170 ml of methanol and 50 ml of acetic acid and hydrogenated over 0.5 g palladium/carbon (10%) for four hours. The catalyst is filtered off and the solvents are removed. The residue is stirred with ether and then a solution of hydrogen chloride In ether Is added. The white precipitate is filtered by suction, washed with ether and dried in vacuo to give 4.65 g of the title compound. The mass spectrum shows the molecular peak MH$^+$ at 194 Da.

B6. Methyl 4-(Hydroxyimino-methyl)cinnamate 4.0 g of methyl 4-formylcinnamate are dissolved in 40 ml methanol and then 1.6 g hydroxylamine-hydrochloride and 1.9 g sodium acetate are added. The mixture is stirred overnight and then diluted with 300 ml water. The precipitate is filtered by suction, dried in vacuo and crystallized from ethyl acetate/petrolether. This gives 3.56 9 of the title compound. The mass spectrum shows the molecular peak MH$^+$ at 206 Da.

C1. 1,5-bis-{2-[4-3-(3-tert-Butoxycarbonylaminomethylphenyl)propionyl)piperazin-1-yl]-2-oxoethyl}perhydro-1,5-diazocin-2,6-dione 0.358 g of 3-(3-tert-butyloxycarbonylaminomethylphenyl)propionic acid (starting material C2), 0.445 ml of triethylamine and 0.485 mg of HBTU are successively dissolved in 3 ml of DMF. After stirring for ten minutes 0.3 9 of 1,5-bis-[2-oxo-2-(piperazin-1-yl)-ethyl]perhydro-1,5-diazocin-2,6-dione dihydrochloride (starting material C5) are added and the mixture is stirred for 24 h at RT. The mixture is diluted with dichloromethane and admixed with water. After phase separation, the organic phase is washed with 1N hydrochloric acid solution, 1N aqueous sodium hydroxide solution and water. After drying over magnesium sulfate, the organic solution is concentrated and the residue is chromatographed over silica gel (dichloromethane/methanol=98:2). Concentration of the pure fractions and drying in vacuo gives 0.1 g of the title compound as a colorless powder. The mass spectrum shows the molecular peaks MH$^+$ and MNa$^+$ at 917 and 939 Da.

C2. 3-(3-tert-Butyloxycarbonylaminomethylphenyl) propionic Acid

To 3.6 g of methyl 3-(3-tert-butyloxycarbonylaminomethylphenyl)propionate (C3) in 36 ml of tetrahydrofurane 14.8 ml of 1N aqueous sodium hydroxide solution are added and the mixture is stirred at RT for 2 days. After neutralization with 14.8 ml 1N hydrochloric acid solution and dilution with water the mixture is extracted three times with ethyl acetate. The combined extracts are dried over magnesium sulfate, filtered and the solvent removed in vacuo to give 3.5 g of the title compound as a brownish oil which solidifies on standing in a refrigerator. The mass spectrum shows the molecular peak MNH$_4^+$ at 297 Da.

C3. Methyl 3-(3-tert-Butyloxycarbonylaminomethylphenyl) proplonate 6.9 g of methyl 3-(3-aminomethylphenyl)propionate hydroacetate (starting material C4) and 9.46 ml of triethylamine are mixed in 75 ml of dichloromethane. To this mixture, 5.94 g of di-tert-butyl-dicarbonate are added in portions with stirring. Stirring is continued for 5 h at RT. Then the reaction mixture is washed twice with 1N hydrochloric acid solution, with sodium hydrogen carbonate solution and water. After drying over magnesium sulfate, the solvent is removed and the residue is chromatographed over silica gel (petrolether/ethyl acetate=7:3). Concentration of the pure fractions and drying in vacuo gives 3.93 g of the title compound as an oil. The mass spectrum shows the molecular peak MNH$_4^+$ at 311 Da.

C4. Methyl 3-(3-Aminomethylphenyl)proplonate Hydroacetate 8.22 g of methyl 3-(3-cyanophenyl)acrylate are hydrogenated in a mixture of 80 ml methanol and 5 ml acetic acid over 0.8 g palladium/carbon(10%) for 20 h. The catalyst is filtered off and the solvent is removed. The residue is coevaporated three times with toluene and dried in vacuo to give 7.5 g of the title compound. The mass spectrum shows the molecular peak MH$^+$ at 194 Da.

C5. 1,5-bis-[2-oxo-2-piperazin-1-yl)-ethyl]perhydro-1,5-diazocin-2,6-dione Dihydrochloride To 2.95 g of 1,5-bis-[2-oxo-2-(4-tert-butyloxycarbonylpiperazin-1-yl)ethyl]perhydro-1,5-diazocin-2,6-dione (starting material C6) in 10 ml dichloromethane 10 ml of trifluoroacetic acid are added with stirring. After four days the mixture is diluted with ether and the title compound is precipitated by addition of a solution of hydrogen chloride in ether. The precipitate is filtered by suction, washed with ether and dried in vacuo to give 2.2 g. The mass spectrum shows the molecular peak MH$^+$ at 395 Da.

C6. 1,5-bis-[2-oxo-2-(4-tert-Butyloxycarbonylpiperazin-1-yl)ethyl]perhydro-1,5-diazocin-2,6-dione 2.5 ml of ethyldiisopropylamine and 4.62 g HBTU are successively added to a solution of 1.5 g of (5-carboxymethyl-2,6-dioxoperhydro-1,5diazocin-1-yl) acetic acid (starting material A2) in 10 ml dimethyifonmamide with stirring. After 15 minutes 2.27 g 1-tert-butoxycarbonylpiperazine are added and the mixture is stirred overnight at RT. After dilution with ethyl acetate and water, the organic phase is separated and washed twice with 1N aqueous sodium hydroxide solution and 1N hydrochloric acid solution and finally with sodium-hydrogen carbonate solution and brine. After drying over magnesium sulfate and filtration, the solvent is removed and the residue is dried under reduced pressure to give 3.1 g of the title compound. The mass spectrum shows the molecular peaks MH$^+$ and MNa$^+$ at 595 and 617 Da.

D1. 1,5-bis-{2-[4-(2-(4-tert-Butoxycarbonylaminophenoxy)-acetyl)piperazin-1-yl]-2-oxoethyl}-1,5-diazocin-2,6-dione 0.5 ml of triethylamine and 0.485 g HBTU are successively added to a solution of 0.36 g of 2-(4-tert-butoxycarbonylaminomethyl-phenoxy)acetic acid (starting material D2) in 3 ml dimethylformamide with stirring. After 15 min 0.3 g of 1,5-bis-[2-oxo-2-(piperazin-1-yl)-ethyl] perhydro-1,5-diazocin-2,6-dione-dihydrochloride (starting material C5) are added and the mixture is stirred for 48 h at RT. The mixture is diluted with dichloromethane and admixed with water. After phase separation, the organic phase is washed twice with 1N aqueous sodium hydroxide solution and 1N hydrochloric acid solution and finally with sodium hydrogen carbonate solution and brine. After drying over magnesium sulfate, the organic solution is concentrated and the residue is chromatographed over silica gel (dichloromethane/methanol=88:12). Concentration of the pure fractions and drying in vacuo gives 0.175 g of the title compound as a powder. The mass spectrum shows the molecular peaks MH$^+$ and MNa$^+$ at 921 and 943 Da.

D2. 2-(4-tert-Butoxycarbonylaminomethyl-phenoxy)acetic Acid 1 g of methyl 2-(4-tert-butoxycarbonylaminomethyl-phenoxy)acetate (starting material D3) is saponified with 4.1 ml 1N aqueous sodium hydroxide solution in 10 ml tetrahydrofurane as described for starting material C2. Yield: 0.7g; the mass spectrum shows the molecular peak MNa$^+$ at 304 Da.

D3. Methyl 2-(4-tert-butoxycarbonylaminomethyl-phenoxy)acetate 21.1 ml of triethylamine are added to a suspension of 14.1 g methyl 2-(4-aminomethyl-phenoxy)-acetate hydrochloride (starting material D4) in 150 ml dichloromethane with stirring, then a solution of 13.93 g of di-tert-butyl-dicarbonate in 30 ml dichloromethane is added dropwise and the mixture is stirred overnight at RT. The reaction mixture is washed twice with 1N aqueous sodium hydroxide solution and 1N hydrochloric acid solution and finally with sodium hydrogen carbonate solution and brine. After drying over magnesium sulfate and filtration, the solvent is removed and the residue is dried under reduced pressure to give 16.7 g of the title compound. The mass spectrum shows the molecular peak MNH$_4^+$ at 313 Da.

D4. Methyl 2-(4-aminomethyl-phenoxy)acetate Hydrochloride

A solution of 18.3 g of methyl 2-(4-hydroxyiminomethyl-phenoxy)acetate (starting material D5) and 45 ml acetic acid in 150 ml methanol is hydrogenated over 2 g palladium/carbon(10%) for 5 h. The catalyst is filtered off and the solvent is removed. The residue is coevaporated three times with toluene and then triturated with a solution of hydrogen chloride in ether. The precipitate formed is filtered by suction, washed several times with ether and dried under reduced pressure to give 15.9 g of the title compound. The mass spectrum shows the molecular peak MH$^+$ at 196 Da.

D5. Methyl 2-(4-Hydroxyiminomethyl-phenoxy)acetate 24.4 g of methyl 2-(4-formylphenoxy)acetate are dissolved in 300 ml methanol and then 9.6 g hydroxylamine hydrochloride and 11.33 g sodium acetate are added. The mixture is stirred overnight, then diluted with 1.2 l water and cooled. The precipitate is filtered off by suction, washed with cold water and dried under reduced pressure. This gives 18.43 g of the title compound. The mass spectrum shows the molecular peak MH$^+$ at 210 Da.

Commercial Utility

As tryptase inhibitors, the compounds according to the invention have useful pharmacological properties which make them commercially utilizable. Human tryptase is a serine protease which is the main protein in human mast cells. Tryptase comprises eight closely related enzymes (α1, α2, β1a, β1b, β2, β3, mMCP-7-like-1, mMCP-7-like-2; 85 to 99% sequence identity) (cf. Miller et al., J. Clin. Invest. 84 (1989) 1188–1195; Miller et al., J. Clin. Invest. 86 (1990) 864–870; Vanderslice et al., Proc. Natl. Sci., USA 87 (1990) 3811–3815; Pallaoro et al., J. Biol. Chem. 274 (1999) 3355–3362). However, only the p-tryptases (Schwartz et al., J. Clin. Invest. 96 (1995) 2702–2710; Sakai et al., J. Clin. Invest. 97 (1996) 988–995) are activated intracellularly and stored in catalytically active form in secretory granules. Compared with other known serine proteases, such as, for example, trypsin or chymotrypsin, tryptase has some special properties (Schwartz et al., Methods Enzymol. 244, (1994), 88–100; G. H. Caughey, "Mast cell proteases in immunology and biology". Marcel Dekker, Inc., New York, 1995). Tryptase from human tissue has a noncovalenuy-linked tetrameric structure which has to be stabilized by heparin or other proteoglycanes to be proteolytically active. Together with other inflammatory mediators, such as, for example, histamine and proteoglycanes, tryptase is released when human mast cells are activated. Because of this, tryptase is thought to play a role in a number of disorders, in particular in allergic and inflammatory disorders, firstly because of the importance of the mast cells in such disorders and secondly since an increased tryptase concentration was observed in a number of disorders of this type. Thus, tryptase is associated, inter alia, with the following diseases: acute and chronic (in particular inflammatory and allergen-induced) airway disorders of various origins (for example bronchitis, alergic bronchitis, bronchial asthma, COPD); interstitial lung disorders; disorders based on allergic reactions of the upper airways, (pharynx, nose) and the adjacent regions (for example paranasal sinuses, conjunctivae), such as, for example allergic conjunctivitis and allergic rhinitis; disorders of the arthritis type (for example rheumatoid arthritis); autoimmune disorders, such as multiple sclerosis; furthermore periodontitis, anaphylaxis, interstitial cystitis, dermatitis, psoriasis, sclerodermia/systemic sclerosis, inflammatory intestinal disorders (Crohn's disease, inflammatory bowel disease) and others. In particular, tryptase seems to be connected directly to the pathogenesis of asthma (Caughey, Am. J. Respir. Cell Mol. Biol. 16 (1997), 621–628; R. Tanaka, "The role of tryptase in allergic inflammation" in: Protease Inhibitors, IBC Library Series, 1979, Chapter 3.3.1–3.3.23).

A further subject of the invention relates to the compounds according to the invention for use in the treatment and/or prophylaxis of diseases, in particular the diseases mentioned.

The invention likewise relates to the use of the compounds according to the invention for preparing medicaments which are employed for the treatment and/or prophylaxis of the diseases mentioned.

Medicaments for the treatment and/or prophylaxis of the diseases mentioned, which contain one or more of the compounds according to the invention, are furthermore a subject of the invention.

The medicaments are prepared by processes which are known per se and familiar to the person skilled in the art. As medicaments, the compounds according to the invention (=active compounds) are either employed as such, or preferably in combination with suitable pharmaceutical excipients, for example in the form of tablets, coated tablets, capsules, suppositories, patches, emulsions, suspension, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, they are either administered directly as a powder (preferably in micronized form) or by nebulization of solutions or suspensions which contain them. With respect to the preparations and administration forms, reference is made, for example, to the details in European Patent 163 965.

For the treatment of dermatoses, the compounds according to the invention are in particular used in the form of those medicaments which are suitable for topical administration. For the preparation of the medicaments, the compounds according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by processes known per se. The dosage of the active compounds in the case of systemic therapy (p.o. or i.v.) is between 0.1 and 10 mg per kilogram per day.

Biological Investigations

The documented pathophysiological effects of mast cell tryptase are caused directly by the enzymatic activity of the protease. Accordingly, they are reduced or blocked by inhibitors which inhibit the enzymatic activity of the tryptase. A suitable measure for the affinity of a reversible inhibitor to the target protease is the equilibrium dissociation constant $K_i$ of the enzyme-inhibitor complex. This $K_i$ value can be determined via the effect of the inhibitor on the tryptase-induced cleavage of a chromogenic peptide-p-nitroanilide substrate or a fluorogenic peptide-aminomethylcoumarin substrate.

Methodology

The dissociation constants for the tryptase-inhibitor complexes are determined under equilibrium conditions in accordance with the general proposals of Bieth (Bieth J G, Pathophysiological Interpretation of kinetic constants of protease inhibitors, Bull. Europ. Physiopath. Resp. 16:183–195, 1980) and the methods of Sommerhoff et al. (Sommerhoff C P et al., A Kazal-type inhibitor of human mast cell tryptase: Isolation from the medical leech Hirudo medicinalis, characterization, and sequence analysis, Biol. Chem. Hoppe-Seyler 375: 685–694, 1994).

Human tryptase is isolated from lung tissue or prepared recombinantly; the specific activity of the protease, determined by titration, is usually greater than 85% of the theoretical value. In the presence of heparin (0.1–50 μg/ml) for stabilizing the protease, constant amounts of the tryptase are incubated with increasing amounts of the inhibitors. After an equilibrium between the reaction partners has formed, the remaining enzyme activity after addition of the peptide-p-nitroanilide substrate tos-Gly-Pro-arg-pNA is determined and the cleavage of the latter is monitored at 405 nm for 3 min. Alternatively, the remaining enzymatic activity can also be determined using fluorogenic substrates. The apparent dissociation constants $K_{iapp}$ (i.e. in the presence of substrate) are subsequently determined by adapting the enzyme rates to the general equation for reversible inhibitors (Morrison J F, Kinetics of the reversible inhibition of enzymecatalyzed reactions by tight-binding inhibitors, Biochim. Biophys. Acta 185, 269–286, 1969) using non-linear regression:

$$V_1 V_0 = 1 - \{E_t + I_t + K_{iapp} - [(E_t + I_t + K_{iapp})^2 - 4E_t I_t]^{1/2}\}/2E_t$$

$V_1$ and $V_0$ are the rates in the presence and absence, respectively, of the inhibitor, and $E_t$ and $I_t$ are the tryptase and inhibitor concentrations, respectively.

The apparent dissociation constants determined for the compounds according to the invention are shown in Table A below, where the numbers of the compounds correspond to the numbers of the compounds in the examples.

Table A

| Inhibition of human tryptase | |
|---|---|
| Compound | $K_{iapp}$ ($\mu$M) |
| 1 | 0.0026 |
| 2 | 0.0012 |
| 3 | 0.0033 |
| 4 | 0.0008 |

What is claimed is:

1. A compound of formula I

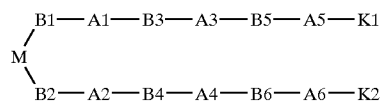

in which

—B1-A1-B3-A3-B5-A5— and —B2-A2-B4-A4-B6-A6— are identical and are selected from the group consisting of

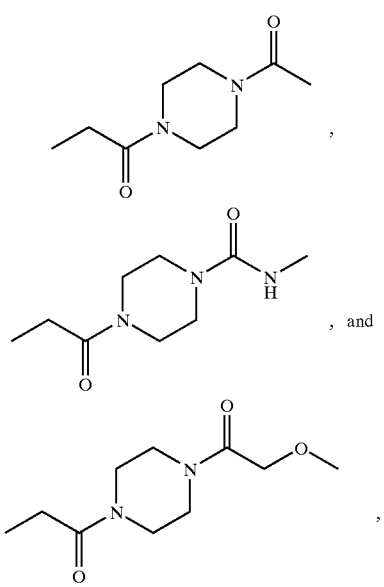

, and

M is the following central building block

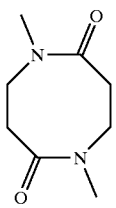

K1 is —B7-(C(C))$_m$—B9-Z1-B11-X1,
K2 is —B8-(C(O))$_p$—B10-Z2-B12-X2,
B7 and B8 are identical and are a bond or methylene,
B9 and B10 are identical and are a bond or methylene,
B11 and B12 are methylene,
m is 0,
p is 0,
X1 and X2 are amino,
Z1 and Z2 are identical and are 1,3-phenylene or 1,4-phenylene, or a salt thereof.

2. A compound of formula I according to claim 1, selected from the group 1,5-bis-{2-[4-[(4-aminomethylbenzylaminocarbonyl) piperazin-1-yl]-2-oxoethyl}-perhydro-1,5-diazocin-2,6-dione;

1,5-bis-{2-[4-(3-(4-aminomethylphenyl)propionyl) piperazin-1-yl]-2-oxoethyl}-perhydro-1,5-diazocin-2,5-dione;

1,5-bis-{2-[4-(3-(3-aminomethylphenyl)propionyl) piperazin-1-yl]-2-oxoethyl}-perhydro-1,5-diazocin-2,6-dione;

1,5-bis-{2-[4-(2-(4-aminomethylphenoxy)acetyl) piperazin-1-yl]-2-oxoethyl}-perhydro-1,5-diazocin-2,6-dione;

or a salt thereof.

3. A method for treating an allergic or inflammatory disorder which comprises:

administering the compound of claim 1 to a patient in need thereof wherein the allergic or inflammatory disorder is selected from the group consisting of bronchitis, allergic bronchitis, asthma, bronchial asthma, COPD, allergic conjunctivitis, allergic rhinitis, arthritis, rheumatoid arthritis, periodontitis, anaphylaxis, interstitial cystitis, dermatitis, psoriasis, sclerodermatitis, Crohn's disease and inflammatory bowel disease, wherein the allergic or inflammatory disorder may be acute or chronic.

4. A pharmaceutical composition comprising one or more compounds of formula I as claimed in claim 1, together with pharmaceutically acceptable auxiliaries and/or excipients.

5. A method of treating an allergic or inflammatory disorder according to claim 3, wherein the allergic or inflammatory disorder is selected from the group consisting of bronchitis, allergic bronchitis, asthma, bronchial asthma, and COPD, wherein the allergic or inflammatory disorder may be acute or chronic.

* * * * *

UNITED STATES PATENT AND TRADEMARK OFFICE
CERTIFICATE OF CORRECTION

PATENT NO. : 6,673,786 B1
DATED : January 6, 2004
INVENTOR(S) : Ulrich

It is certified that error appears in the above-identified patent and that said Letters Patent is hereby corrected as shown below:

Column 26,
Line 12, change "K1 is — B7-$(C(C))_m$ — B9-Z1-B11-X1," to
-- K1 is — B7-$(C(O))_m$ — B9-Z1-B11-X1, --.

Signed and Sealed this

Thirteenth Day of April, 2004

JON W. DUDAS
*Acting Director of the United States Patent and Trademark Office*